(12) United States Patent
Jones (10) Patent No.: US 10,279,091 B1
(45) Date of Patent: May 7, 2019

(54) PROGRESSIVE SEQUENCING LACTATING BREAST MILK EXTRACTION APPARATUS AND METHOD OF USE

(71) Applicant: Jennifer Jones, Boca Raton, FL (US)

(72) Inventor: Jennifer Jones, Boca Raton, FL (US)

(*) Notice: Subject to any disclaimer, the term of this patent is extended or adjusted under 35 U.S.C. 154(b) by 541 days.

(21) Appl. No.: 14/960,357

(22) Filed: Dec. 5, 2015

Related U.S. Application Data

(62) Division of application No. 14/806,589, filed on Jul. 22, 2015.

(60) Provisional application No. 62/195,270, filed on Jul. 21, 2015, provisional application No. 62/088,904, filed on Dec. 8, 2014, provisional application No. 62/027,693, filed on Jul. 22, 2014.

(51) Int. Cl.
*A61M 1/00* (2006.01)
*A61M 1/06* (2006.01)
*A61M 1/10* (2006.01)

(52) U.S. Cl.
CPC .......... *A61M 1/064* (2014.02); *A61M 1/1039* (2014.02); *A61M 2205/106* (2013.01)

(58) Field of Classification Search
CPC ...... A61M 1/062; A61M 1/064; A61M 1/066; A61M 1/06; A61B 5/4288; A61B 10/0041
See application file for complete search history.

(56) References Cited

U.S. PATENT DOCUMENTS

| | | | |
|---|---|---|---|
| 3,035,571 A | 5/1962 | Jones | |
| 4,740,196 A | 4/1988 | Powell | |
| 6,273,868 B1 | 8/2001 | Nordvik | |
| 2004/0087898 A1 | 5/2004 | Weniger | |
| 2006/0106334 A1* | 5/2006 | Jordan | A61M 1/0027 604/74 |
| 2015/0065994 A1* | 3/2015 | Fridman | A61M 1/06 604/514 |

* cited by examiner

*Primary Examiner* — Nathan R Price
*Assistant Examiner* — Justin L Zamory
(74) *Attorney, Agent, or Firm* — Allen D Hertz, P.A.; Allen D. Hertz (57) ABSTRACT

A progressive sequencing lactating breast milk extraction apparatus comprising a series of compression segments arranged forming a conical shape extending between a wider chest end and a narrower extracted milk collection end, at least one vibration generating apparatus in vibrational communication with at least one compression segment of the series of compression segments; and an operational mechanism to contract and expand each compression segment. In use, the operational mechanism cycles each compression segment of the series of compression segments between a compressed state and a relaxed state and the cycles are provided sequentially from a rear of the progressive sequencing lactating breast milk extraction apparatus to the extracted milk collection end. The vibrational energy applied to the breast aids in flow of the milk through the breast.

20 Claims, 6 Drawing Sheets

PROGRESSIVE SEQUENCING LACTATING BREAST MILK EXTRACTION APPARATUS AND METHOD OF USE

RELATED US PATENT APPLICATIONS

This Non-Provisional patent application is a Divisional patent application claiming the benefit of:
co-pending U.S. Non-Provisional patent application Ser. No. 14/806,589, filed on Jul. 22, 2015 which claims the benefit of each of:
U.S. Provisional Patent Application Ser. 62/195,270, filed on Jul. 21, 2015,
U.S. Provisional Patent Application Ser. 62/088,904, filed on Dec. 8, 2014, and
U.S. Provisional Patent Application Ser. 62/027,693, filed on Jul. 22, 2014,
all of which are incorporated into this Non-Provisional patent application in their entireties by reference.

FIELD OF THE INVENTION

The present invention relates to a woman's breast milk extraction apparatus and method of use. More specifically, the woman's breast milk extraction apparatus includes a series of compression bands and a vibration mechanism.

BACKGROUND OF THE INVENTION

Breast pumps are mechanical devices that extract milk from the breasts of a lactating woman. Breast pumps may be manually powered or electrical powered. Breast pumps extract breast milk by creating and applying a vacuum to the woman's breast. This process causes short and long term discomfort to the user.

Breastmilk is milk produced by the breasts (or mammary glands) of a human female for her infant offspring. Breastmilk is the most superior primary source of nutrition for newborns before they are able to eat and digest other foods; older infants around six months of age and toddlers may continue to be breastfed, in combination with other foods when solid foods may be introduced.

Breastmilk offers benefits for both mother and baby. Breastmilk is easy for the baby to digest, which promotes more frequent eating due to faster digestion. It is associated with a decrease risk of diabetes and celiac disease. Benefits for the mother include better uterine shrinkage, decreased risk of breast cancer and postpartum depression. It may also be a bonding experience for mother and child, and can be less expensive than infant formula. Breastfeeding may also decrease the risk of obesity in adulthood and improved cognitive development.

To maintain a continued process of feeding an infant or child breastmilk in an infant condition/situation where breastfeeding would be unavailable (for any reason) or a maternal condition/situation where extraction of breastmilk is necessary or stimulation to increase or management of decreasing a milk supply is desired or mobilization of sedentary breastmilk (in the case of plugged ducts, mastitis, breast abscess) is necessary, the mother would utilize a breast pump to extract breastmilk from the breast and store the extracted breastmilk for feeding later using a bottle or other implement.

The production and lactation process employs glands and ducts. Lactation describes the secretion of breastmilk from the mammary glands and the period of time that a mother lactates to feed her young. The process can occur with almost all post-pregnancy female mammals, although it predates mammals. In humans the process of feeding breastmilk is also called breastfeeding or nursing.

Breastfeeding or other breastmilk delivery processes can encounter any of a number of issues. It is common for many women to have engorgement and/or a plugged duct at some point breastfeeding. Engorgement is a painful condition of breast congestion due to a failure to properly breastfeed or overproduction of milk supply. A plugged milk duct feels like a tender and sore lump in the breast. It is not accompanied by a fever or other symptoms. It happens when a milk duct does not properly drain and becomes inflamed. Then, pressure builds up behind the plug, and surrounding tissue becomes inflamed. A plugged duct usually only occurs in one breast at a time. In some instances, a ducted duct may turn into a breast infection called mastitis and in severe cases, may lead to breast abscess.

Therefore, a process enhancing a process of producing, increasing or managing a decrease in breastmilk production, and/or mobilizing/extracting/collecting breastmilk from a breast is desired. The desired process should be effective while remaining comfortable to the user.

SUMMARY OF THE INVENTION

The present invention overcomes the deficiencies of the known art by disclosing an apparatus and a method for extracting breast milk from a woman, wherein the apparatus would be effective while remaining comfortable to the user.

In accordance with one embodiment of the present invention, the invention consists of a progressive sequencing lactating breast milk extraction apparatus comprising:
    a series of compression segments arranged forming a conical shape extending between a wider chest end and a narrower extracted milk collection end;
    at least one vibration generating apparatus in vibrational communication with at least one compression segment of the series of compression segments; and
    an operational mechanism, wherein the operational mechanism cycles each compression segment of the series of compression segments between a compressed state and a relaxed state and the cycles are provided sequentially from a rear of the progressive sequencing lactating breast milk extraction apparatus to the extracted milk collection end.

In a second aspect, the progressive sequencing lactating breast milk extraction apparatus further comprises an operational controller. The operational controller includes a microprocessor, a memory device, a power source, and any other components required to support operation of the progressive sequencing lactating breast milk extraction apparatus. The operational controller would be in communication with the operational mechanism and each at least one vibration generating apparatus.

In another aspect, each compression segment of the series of compression segments can be cycled by collecting and releasing a compression segment controlling element, wherein the compression segment controlling element can be a strap or other continuous element circumscribing the associated compression segment.

In yet another aspect, each operational mechanism can include a rotating element, such as a compression segment collection wheel. The compression segment collection wheel can be integrated within a compression actuator housing. The collected portion of the associated compression segment can be stored within the compression actuator housing.

In yet another aspect, each operational mechanism can include a cam, wherein the cam rotates cycling each compression segment between a short circumferential dimension and a long circumferential dimension. The cams can be operated by individual motors, a single drive shaft, a series of gears, and the like.

In yet another aspect, each compression segment of the series of compression segments can be cycled by filling and extracting a volume of gas into a from a gas chamber. The gas chamber would substantially circumscribed the associated compression segment.

In yet another aspect, the series of compression segments can be cycled in a sequential pattern.

In yet another aspect, the series of compression segments can be cycled in a sequential pattern, wherein the sequence operates from a segment proximate a chest of the user towards a nipple of the user.

In yet another aspect, the series of compression segments can be cycled simultaneously.

In yet another aspect, the series of compression segments can be applied to a single breast and cycled accordingly.

In yet another aspect, a pair of series of compression segments can be employed, applying one of the pair to each respective breast.

In yet another aspect, a pair of series of compression segments can be employed, applying one of the pair to each respective breast and operated independent of one another.

In yet another aspect, a pair of series of compression segments can be employed, applying one of the pair to each respective breast and operated simultaneously.

In yet another aspect, a pair of series of compression segments can be employed, applying one of the pair to each respective breast and operated in an alternating pattern.

In yet another aspect, the at least one vibration generating apparatus is provided in a form of a ring.

In yet another aspect, the at least one vibration generating apparatus is provided in a form of a series of rings, each ring being integrated between adjacent compression segments of the series of compression segments.

In yet another aspect, the progressive sequencing lactating breast milk extraction apparatus further comprises a milk collecting breast shield. The milk collecting breast shield can be integrated into the progressive sequencing lactating breast milk extraction apparatus, removably attached to the progressive sequencing lactating breast milk extraction apparatus, or inserted between the progressive sequencing lactating breast milk extraction apparatus and the woman's breast.

In another aspect, each compression segment of the series of compression segments comprises a compression segment compliant element. The compression compliant element can fabricated of a padded material, a silicone, a rubber, a foam, a polyester fill, and the like.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

Detailed embodiments of the present invention are disclosed herein. It will be understood that the disclosed embodiments are merely exemplary of the invention that may be embodied in various and alternative forms. The figures are not necessarily to scale, and some features may be exaggerated or minimized to show details of particular embodiments, features, or elements. Specific structural and functional details, dimensions, or shapes disclosed herein are not limiting but serve as a basis for the claims and for teaching a person of ordinary skill in the art the described and claimed features of embodiments of the present invention. The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims.

Figure 1:
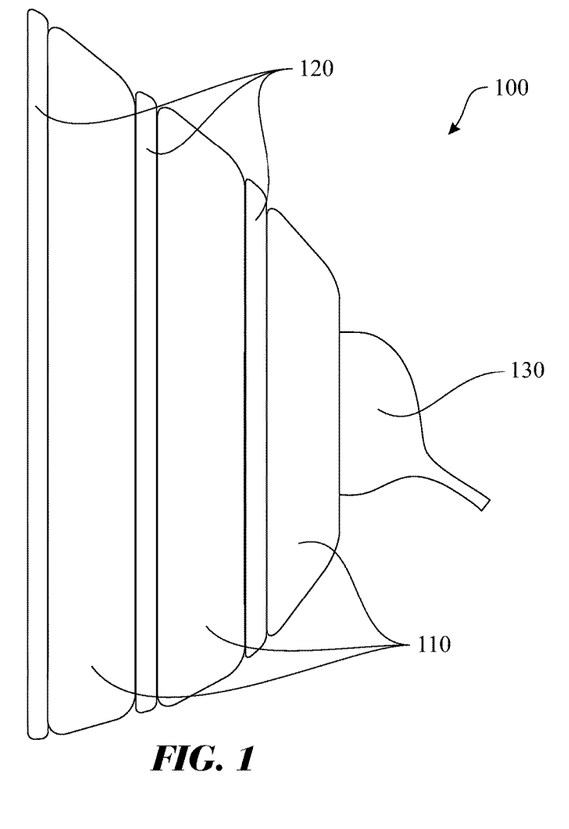
FIG. 1 presents a side view of an exemplary progressive sequencing lactating breast milk extraction apparatus.
Figure 2:
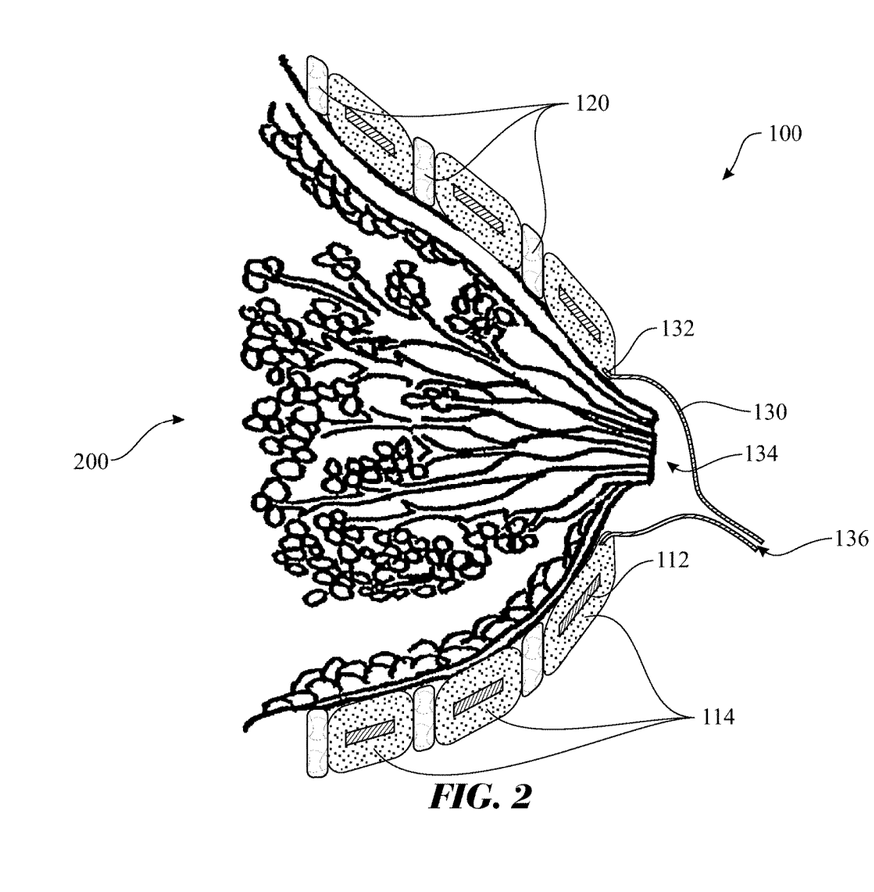
FIG. 2 presents a sectioned side view of the progressive sequencing lactating breast milk extraction apparatus.
Figure 3:
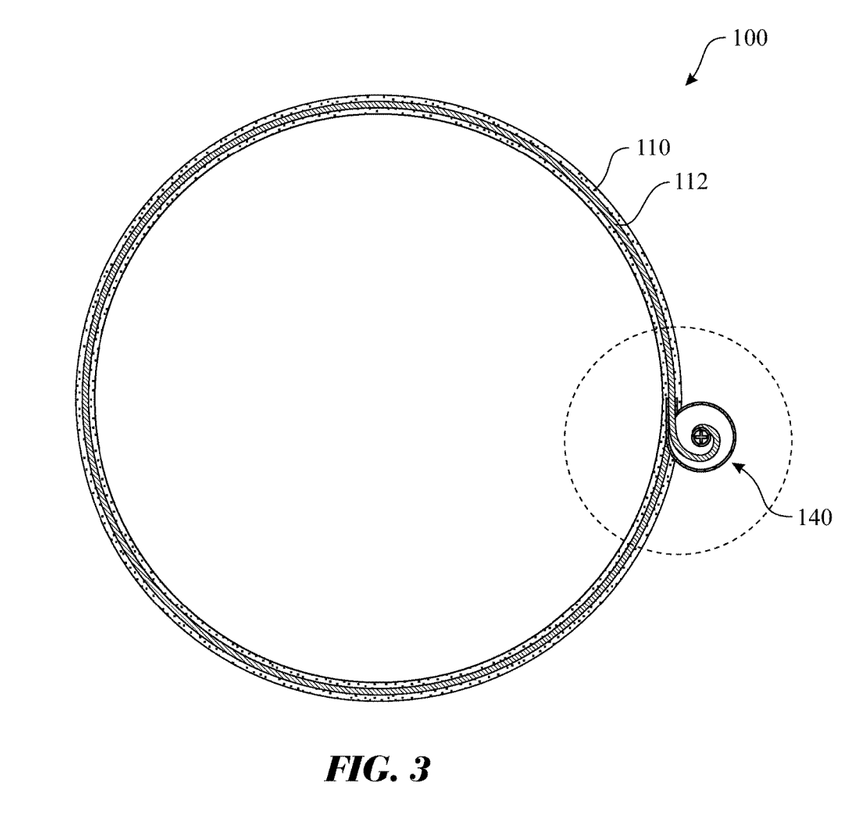
FIG. 3 presents a sectioned front view of the progressive sequencing lactating breast milk extraction apparatus.
Figure 4:
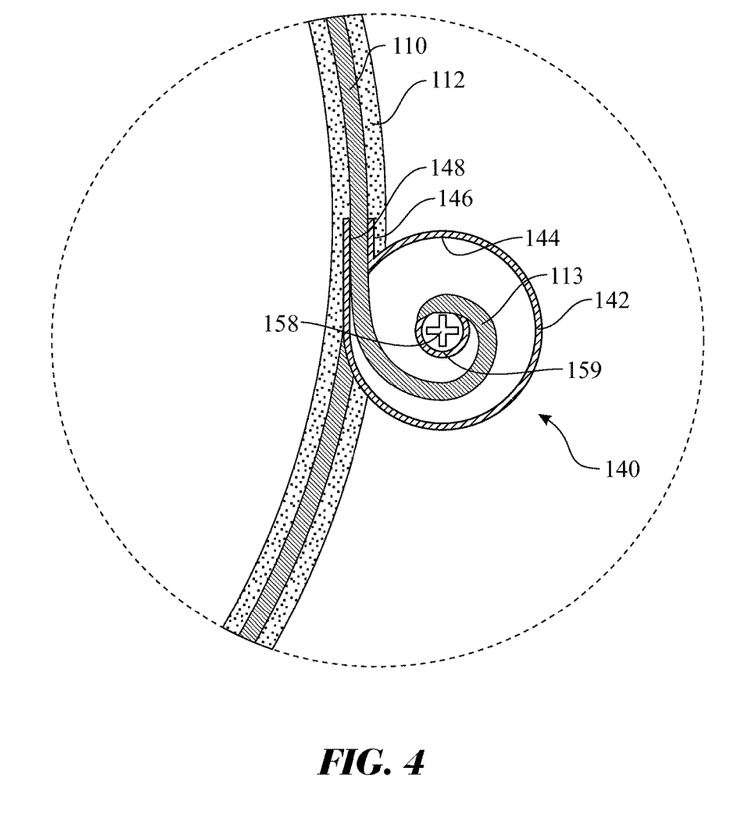
FIG. 4 presents an enlarged sectioned front view of the progressive sequencing lactating breast milk extraction apparatus detailing a compression actuator unit.
Figure 5:
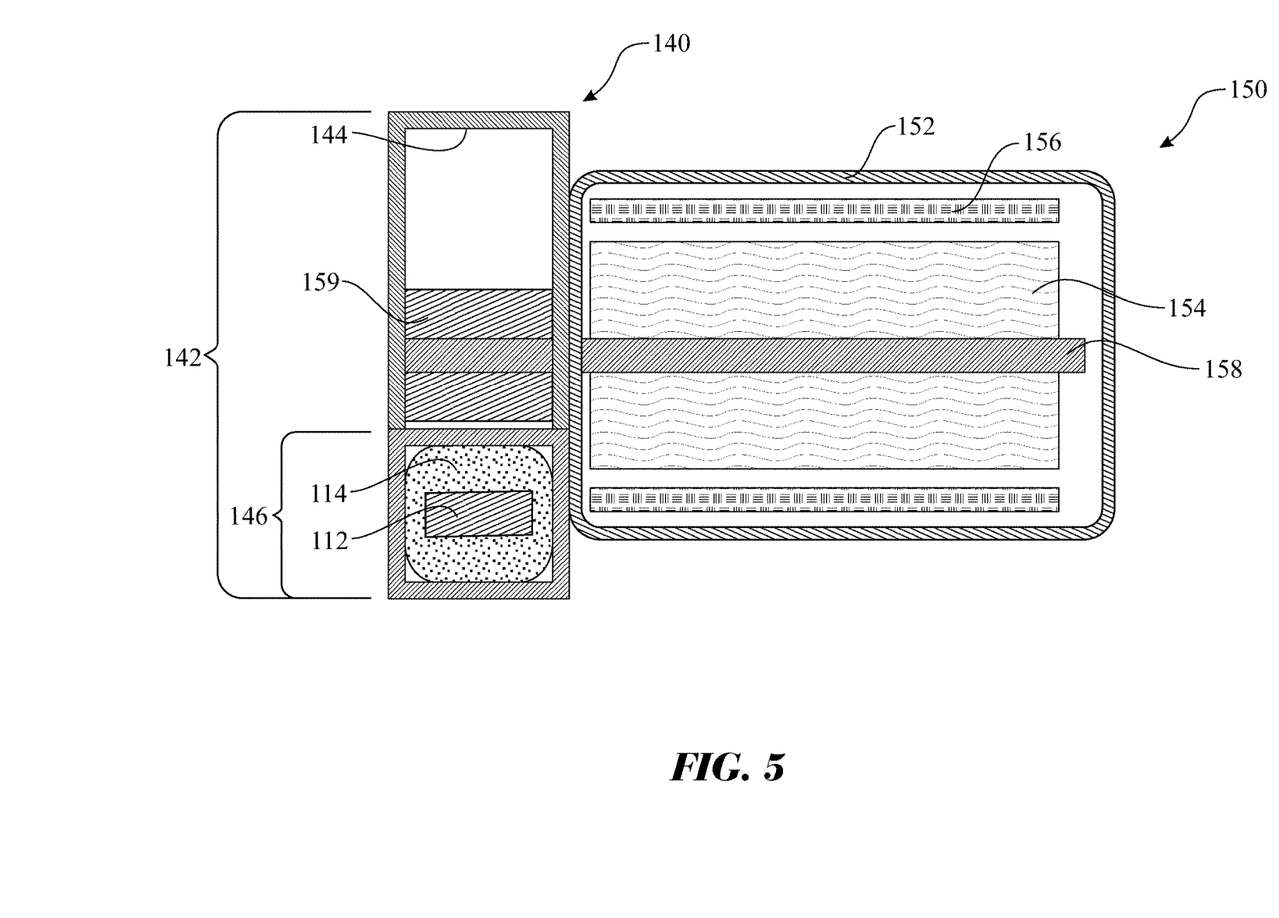
FIG. 5 presents a sectioned side view of the progressive sequencing lactating breast milk extraction apparatus detailing a compression actuator unit.

For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

A progressive sequencing lactating breast milk extraction apparatus 100, as shown in the exemplary embodiment illustrated in FIGS. 1 through 5, provides a comfortable and simple process for extracting milk from a woman's lactating breast 200. The progressive sequencing lactating breast milk extraction apparatus 100 includes a series of compression segments 110 joined with one another forming a generally conical shape. The progressive sequencing lactating breast milk extraction apparatus 100 is shaped having a larger diameter end located proximate a user's chest and a smaller diameter end for collection of extracted milk. A milk collecting breast shield 130 is a funnel shaped element located at the extracted milk collection end. A milk collecting breast shield 130 would preferably be fabricated of a soft, flexible material. The milk collecting breast shield 130 can be integrated into the adjacent compression segment 110, removably attached to the adjacent compression segment 110, or placed between an interior surface of the compression segment 110 and the woman's lactating breast 200. A milk collecting breast shield flange 132 can be formed within an attachment end of the milk collecting breast shield 130 for seating against the woman's lactating breast 200, attachment to the compression segment 110, or any other suitable seating and/or sealing function. The milk collecting breast shield 130 defines a milk collecting breast shield interior volume 134. The extracted milk collects within the milk collecting breast shield interior volume 134 and is directed through a breast shield dispensing conduit 136 for dispensing. The milk collecting breast shield 130 can be fabricated of any suitable material, including plastic, silicone, nylon, and the like. It is preferred that the milk collecting breast shield 130 be fabricated of a translucent or transparent material.

The progressive sequencing lactating breast milk extraction apparatus 100 provides two features for operation: a sequential compression and a vibration. The sequential compression is provided by a series of compression segments 110. Each compression segment 110 includes a feature enabling cycling between a compression condition and a relaxed condition. This cycling can be accomplished by any of a number of processes. The exemplary embodiment employs a compression segment controlling strap 112 embedded within a compression segment compliant element 114, wherein the compression segment controlling strap 112 is retracted by collecting a collected compression segment controlling strap 113 within a compression actuator unit 140 (FIGS. 3 and 4) and expanded by releasing the collected compression segment controlling strap 113 from the compression actuator unit 140. It is understood that the design can utilize compressibility of the compression segment compliant element 114, a gap in the compression segment compliant element 114, or any other design consideration to accommodate the collection of the compression segment controlling strap 112. Alternatively, the compression segment compliant element 114 can be collected in conjunction with the compression segment controlling strap 112. Details of the compression actuator unit 140 are presented in FIGS. 4 and 5. The exemplary compression actuator unit 140 is operated by rotating a compression segment collection wheel 159 within a compression actuator housing 142. In the exemplary embodiment, the rotation is provided by rotating a actuator control motor shaft 158. It is understood that other configurations can be employed to drive the rotation of the compression segment collection wheel 159, such as gears or any other direct or indirect torque applying mechanism. The actuator control motor shaft 158 can be driven by any direct or indirect torque applying mechanism, such as a motor (as shown), one or more gears, a transmission, and the like. The motor 150 includes a actuator control motor rotor 154 assembled to the actuator control motor shaft 158 and a actuator control motor stator 156 affixed to a actuator control motor housing 152. Electrical power is provided to the compression actuator control motor 150 from an operational controller (not shown). The operational controller includes a microprocessor, a memory device, a digital operating instruction set, and a power source (either an integrated portable power supply or a power cable obtaining power from an external power source). The operational controller can be integrated into the progressive sequencing lactating breast milk extraction apparatus 100 or provided as a separate unit that can be worn on a user's waist, clipped onto another object, and the like. The compression actuator control motor 150 is driven in a first direction to collect a collected compression segment controlling strap 113 of the compression segment controlling strap 112, causing the compression segment 110 to compress the woman's lactating breast 200. The compression segment controlling strap 112 is guided into the compression actuator housing interior 144 of the compression actuator unit 140 through a actuator housing compression segment passageway 148 defined by a actuator housing compression segment tangential conduit 146. The torque is removed from the compression segment collection wheel 159 and the resiliency of the woman's lactating breast 200 draws the collected compression segment controlling strap 113 from the compression actuator unit 140. The collected compression segment controlling strap 113 returns through the actuator housing compression segment passageway 148. The operational controller directs the sequential aspect of the process against each compression segment 110 of the series of compression segments 110. The sequence would run from the widest compression segment 110 to the narrowest compression segment 110 in a manner which draws the milk from the woman's lactating breast 200. The extracted milk is then collected in the milk collecting breast shield interior volume 134 of the milk collecting breast shield 130. The collected milk passes through the breast shield dispensing conduit 136 to a bottle, a collection bag, or any other appropriate storage container.

One key result of the compression cycling process is an extraction of milk from the lactating breast. A second result is a reduction of milk congestion within the lactating breast, more specifically, within any distended ducts.

Figure 6:
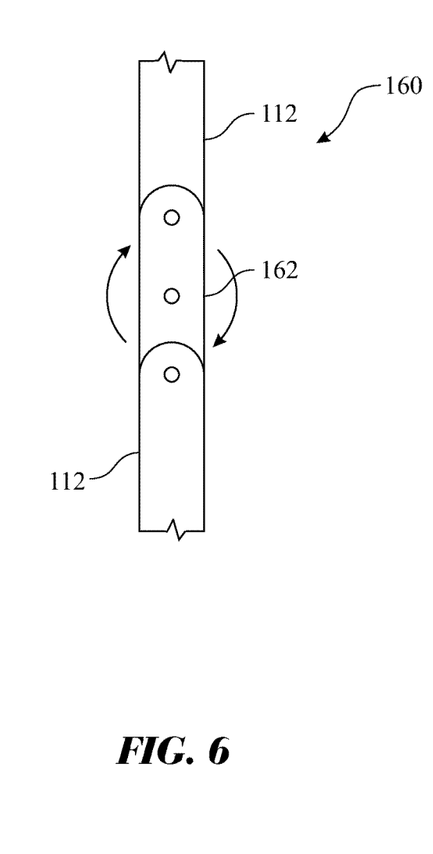
FIG. 6 presents a plan view of an alternative operational mechanism for compressing and relaxing a compression segment of the progressive sequencing lactating breast milk extraction apparatus, the view shown in the relaxed state.
Figure 7:
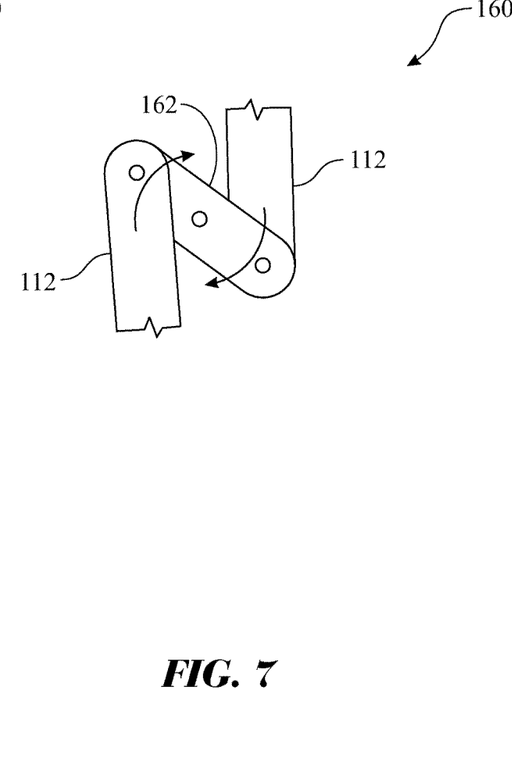
FIG. 7 presents a plan view of the alternative operational mechanism introduced in FIG. 6, the view shown rotating towards the compressing state.

In one alternate configuration, the compression and relaxed cycling process of the compression segment 110 can be accomplished using a rotating element 160, as illustrated in FIGS. 6 and 7. A rotating cam element 162 of the rotating cam system 160 would be rotated into a relaxed state wherein the rotating cam element 162 provides an extension between ends of the compression segment controlling strap 112, effectively increasing a length of the compression segment controlling strap 112. The rotating cam element 162 would continue to rotate into a compression state wherein the rotating cam element 162 positions ends of the compression segment controlling strap 112 in an overlapping state, effectively reducing the length of the compression segment controlling strap 112. The effectively reduced length of the compression segment controlling strap 112 creates the compression, whereas the effectively increased length of the compression segment controlling strap 112 provides the relaxed state. The process is sequenced between each of the compression segments 110 to draw milk from the woman's lactating breast 200.

In another alternate configuration, the compression and relaxed cycling process of the compression segment 110 can be accomplished using a pneumatic system. The compression segment controlling strap 112 would be replaced with an air bladder. The pneumatic system fills the air bladder with a gas (preferably air) to place the compression segment 110 into a compression state. The pneumatic system removes the gas from the air bladder to place the compression segment 110 into a relaxed state. The process is sequenced between each of the compression segments 110 to draw milk from the woman's lactating breast 200.

A vibration is introduced by each vibration segment 120. The vibration segment 120 can be of any suitable vibration producing element or series of elements. The vibration breaks apart any congestion of the milk, reduces impact of surface tension, and aids in flow of the milk towards the nipple. In the exemplary embodiment, one vibration segment 120 is integrated between two adjacent compression segments 110. Each vibration segment 120 is formed as a partial or complete ring. Alternatively, the vibration segment 120 can be any vibration producing component that applies a vibration to the woman's lactating breast 200. The vibration segment 120 can also be placed at either or both ends of the progressive sequencing lactating breast milk extraction apparatus 100. The vibrational energy can be provided in a sequence with the compression cycles, parallel to the compression cycles, randomly, continuously, or in accordance with any other pattern. The compression cycles can be provided sequentially from the rear of the progressive sequencing lactating breast milk extraction apparatus to the extracted milk collection front end or sequentially from the extracted milk collection front end of the progressive sequencing lactating breast milk extraction apparatus to the rear of the progressive sequencing lactating breast milk extraction apparatus. It is understood that different patterns of compression cycles can be combined during use or over time.

The progressive sequencing lactating breast milk extraction apparatus 100 can be offered in a variety of cup sizes to optimize a fit to the user's lactating breast 200. The progressive sequencing lactating breast milk extraction apparatus 100 can be adapted for placement within a bra or bra-like garment, a vest, a tube-top styled garment, or any other suitable wearable device. Alternatively, the sequencing lactating breast milk extraction apparatus 100 can be integrated into a bra or bra-like garment, a vest, or any other suitable wearable device.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

ELEMENT DESCRIPTION REFERENCES

Ref No. Description 100 progressive sequencing lactating breast milk extraction apparatus
110 compression segment
112 compression segment controlling strap
113 collected compression segment controlling strap
114 compression segment compliant element
120 vibration segment
130 milk collecting breast shield
132 milk collecting breast shield flange
134 milk collecting breast shield interior volume
136 breast shield dispensing conduit
140 compression actuator unit
142 compression actuator housing
144 compression actuator housing interior
146 actuator housing compression segment tangential conduit
148 actuator housing compression segment passageway
150 compression actuator control motor
152 actuator control motor housing
154 actuator control motor rotor
156 actuator control motor stator
158 actuator control motor shaft
159 compression segment collection wheel
160 rotating cam system
162 rotating cam element
200 woman's lactating breast

What is claimed is:
1. A method of progressively sequencing a lactating breast for extraction of milk, the method comprising steps of:
placing a progressive sequencing lactating breast milk extraction apparatus upon a lactating breast, the progressive sequencing lactating breast milk extraction apparatus comprising:
a series of compression segments arranged forming a conical shape extending between a wider, chest rear end and a narrower, extracted milk collection front end,
each compression segment of the series of compression segments is formed of a pliant tubular material having a substantially continuous annular shape wherein an exterior surface of the annular shape defines an annular shaped interior opening, the annular shaped interior opening being sized to contact and substantially circumscribe the lactating breast, each of the series of compression segments having a hollow passageway passing through an interior of each compression segment of the series of compression segments,
a plurality of compression segment controlling straps, each compression segment controlling strap of the plurality of compression segment controlling straps extending through and encased within the hollow passageway within the interior of each respective compression segment, and
an operational mechanism that toggles a respective compression segment controlling strap of the plurality of compression segment controlling straps between a contracted state and an expanded state;
actuating the operational mechanism to cycles each compression segment controlling strap of the plurality of compression segment controlling straps between a compressed state and a relaxed state, thus cycling each compression segment of the series of compression segments between a compressed state and a relaxed state.
2. A method of progressively sequencing a lactating breast for extraction of milk as recited in claim 1, wherein the step of cycling each compression segment of the series of compression segments between a compressed state and a relaxed state is accomplished in at least one of:
simultaneously,
randomly,
sequentially from the rear of the progressive sequencing lactating breast milk extraction apparatus to the extracted milk collection front end, and
sequentially from the extracted milk collection front end of the progressive sequencing lactating breast milk extraction apparatus to the rear of the progressive sequencing lactating breast milk extraction apparatus.

3. A method of progressively sequencing a lactating breast for extraction of milk as recited in claim 1, further comprising a step of:
applying vibrational energy to the lactating breast.

4. A method of progressively sequencing a lactating breast for extraction of milk as recited in claim 1, further comprising a step of:
applying vibrational energy to the lactating breast during the step of applying a compression to the lactating breast.

5. A method of progressively sequencing a lactating breast for extraction of milk as recited in claim 1, wherein the step of retracting and expanding the compression segment controlling strap is actuated by a rotating motion and a counter-rotating motion of a shaft of a compression actuator control motor.

6. A method of progressively sequencing a lactating breast for extraction of milk as recited in claim 1, wherein the step of retracting and expanding the compression segment controlling strap is actuated by a rotating and counter-rotating motion of a shaft of a compression actuator control motor, wherein the compression segment controlling strap is collected upon the shaft of a compression actuator control motor during a rotating motion of the shaft and wherein the compression segment controlling strap is released from the shaft of the compression actuator control motor during the counter-rotating motion of the shaft.

7. A method of progressively sequencing a lactating breast for extraction of milk as recited in claim 1, wherein the step of retracting and expanding the compression segment controlling strap is actuated by a rotating motion of a shaft of a compression actuator control motor.

8. A method of progressively sequencing a lactating breast for extraction of milk as recited in claim 1, wherein the step of retracting and expanding the compression segment controlling strap is actuated by a rotating motion of a rotating cam element.

9. A method of progressively sequencing a lactating breast for extraction of milk as recited in claim 1, wherein the pliant material is at least one of:
(a) a padded material,
(b) a silicone,
(c) a rubber,
(d) a foam, and
(e) a polyester fill.

10. A method of progressively sequencing a lactating breast for extraction of milk, the method comprising steps of:
placing a progressive sequencing lactating breast milk extraction apparatus upon a lactating breast, the progressive sequencing lactating breast milk extraction apparatus comprising:
a series of compression segments arranged forming a conical shape extending between a wider, chest rear end and a narrower, extracted milk collection front end,
each compression segment of the series of compression segments is formed of a pliant material having a continuous circular shape wherein an exterior of the shape defines an opening, the opening being sized to fit around the lactating breast, each of the series of compression segments having a hollow passageway passing through an interior of each compression segment of the series of compression segments,
a plurality of compression segment controlling straps, each compression segment controlling strap of the plurality of compression segment controlling straps extending through and encased within the hollow passageway within the interior of each respective compression segment,
at least one vibration segment, each vibration segment having an annular shape to circumscribe the lactating breast, each vibration segment of the at least one vibration segment being located between two adjacent compression segments, and
an operational mechanism that toggles a respective compression segment controlling strap of the plurality of compression segment controlling straps between a contracted state and an expanded state;
actuating the operational mechanism to cycles each compression segment controlling strap of the plurality of compression segment controlling straps between a compressed state and a relaxed state, thus cycling each compression segment of the series of compression segments between a compressed state and a relaxed state.

11. A method of progressively sequencing a lactating breast for extraction of milk as recited in claim 10, wherein the step of cycling each compression segment of the series of compression segments between a compressed state and a relaxed state is accomplished in at least one of:
simultaneously,
randomly,
sequentially from the rear of the progressive sequencing lactating breast milk extraction apparatus to the extracted milk collection front end, and
sequentially from the extracted milk collection front end of the progressive sequencing lactating breast milk extraction apparatus to the rear of the progressive sequencing lactating breast milk extraction apparatus.

12. A method of progressively sequencing a lactating breast for extraction of milk as recited in claim 10, further comprising a step of:
applying vibrational energy to the lactating breast.

13. A method of progressively sequencing a lactating breast for extraction of milk as recited in claim 10, further comprising a step of:
applying vibrational energy to the lactating breast during the step of applying a compression to the lactating breast.

14. A method of progressively sequencing a lactating breast for extraction of milk as recited in claim 10, wherein the step of retracting and expanding the compression segment controlling strap is actuated by a rotating motion of a shaft of a compression actuator control motor.

15. A method of progressively sequencing a lactating breast for extraction of milk as recited in claim 10, wherein the step of retracting and expanding the compression segment controlling strap is actuated by a rotating motion of a rotating cam element.

16. A method of progressively sequencing a lactating breast for extraction of milk as recited in claim 10, wherein the pliant material is at least one of:
(a) a padded material,
(b) a silicone,
(c) a rubber,
(d) a foam, and
(e) a polyester fill.

17. A method of progressively sequencing a lactating breast for extraction of milk, the method comprising steps of:

placing a progressive sequencing lactating breast milk extraction apparatus upon a lactating breast, the progressive sequencing lactating breast milk extraction apparatus comprising:
- a series of compression segments arranged forming a conical shape extending between a wider, chest rear end and a narrower, extracted milk collection front end, each compression segment of the series of compression segments is configured to solely cycle between a compressed state and a relaxed state,
- at least one vibration segment, each vibration segment having an annular shape to circumscribe the lactating breast, each vibration segment of the at least one vibration segment being located between two adjacent compression segments, each vibration segment of the at least one vibration segment is configured to solely apply vibrational energy, and
- an operational mechanism;

cycling each compression segment of the series of compression segments between the compressed state and a relaxed state; and activating the at least one vibration segment, applying the vibrational energy to the lactating breast.

18. A method of progressively sequencing a lactating breast for extraction of milk as recited in claim 17, wherein the step of cycling each compression segment of the series of compression segments between a compressed state and a relaxed state is accomplished in at least one of:
- simultaneously,
- randomly,
- sequentially from the rear of the progressive sequencing lactating breast milk extraction apparatus to the extracted milk collection front end, and
- sequentially from the extracted milk collection front end of the progressive sequencing lactating breast milk extraction apparatus to the rear of the progressive sequencing lactating breast milk extraction apparatus.

19. A method of progressively sequencing a lactating breast for extraction of milk as recited in claim 17, wherein the step of cycling each compression segment of the series of compression segments between a compressed state and a relaxed state is accomplished by retracting and expanding a compression segment controlling strap, wherein the compression segment controlling strap is integral with the compression segment.

20. A method of progressively sequencing a lactating breast for extraction of milk as recited in claim 17, further comprising a step of providing a compliant element between each said compression segment of said series of compression segments and said lactating breast.

* * * * *